United States Patent [19]

Egerer et al.

[11] Patent Number: 5,434,187
[45] Date of Patent: Jul. 18, 1995

[54] EYE DROPS

[76] Inventors: Ido Egerer, Niedermarkt 24, A-3400 Klosterneuburg; Johannes Menzel, Stallburggasse 4/19, A-1010 Wien, both of Austria

[21] Appl. No.: 852,172

[22] Filed: May 19, 1992

[30] Foreign Application Priority Data

Oct. 4, 1989 [AT] Austria .................... 2298/89

[51] Int. Cl.$^6$ .................................... A61K 31/19
[52] U.S. Cl. ............................ 514/574; 514/912
[58] Field of Search ........................ 514/574, 912

[56] References Cited

U.S. PATENT DOCUMENTS

| | | |
|---|---|---|
| 4,034,077 | 7/1977 | Hill et al. ........................ 424/69 |
| 4,292,326 | 9/1981 | Nazarro-Porro ................ 424/317 |

FOREIGN PATENT DOCUMENTS

| | | |
|---|---|---|
| 0187433 | 7/1986 | European Pat. Off. . |
| 0229654 | 7/1987 | European Pat. Off. . |
| 0288659 | 11/1988 | European Pat. Off. . |
| WO88/00465 | 1/1988 | WIPO . |

OTHER PUBLICATIONS

Mingrone, G. et al., "Distribution of radiolabelled azelaic acid in eye membranes and fluids of rabbits", 1--Pharmacology vol. 100, 1984, p. 9.

*Primary Examiner*—Zohreh Fay
*Attorney, Agent, or Firm*—Spencer, Frank & Schneider

[57] ABSTRACT

Adding an aliphatic dicarboxylic acid or a salt thereof with an inorganic base to a conventional eye drop solution has been found to extend the dwell time of the solution when applied to the surface of the eye. Thus, Applicants' method of extending dwell time of conventional eye drops applied on the surface of an eye, includes providing an eye drop solution with an additive in an amount effective to extend the dwell time of the eye drop solution on the surface of an eye, the additive including at least one substance selected from the group consisting of an aliphatic dicarboxylic acid having a general formula $(CH_2)_{6-9}.(COOH)_2$ and a salt of an aliphatic dicarboxylic acid having a general formula $(CH_2)_{6-9}.(COOH)_2$ with an inorganic base.

7 Claims, No Drawings

EYE DROPS

BACKGROUND OF THE INVENTION

The present invention belongs to the field of eye drops and is based on the discovery that an addition of aliphatic dicarboxylic acids to eye drops is able to extend the period of dwell of the drops on the surface of the eye. The addition of dicarboxylic acids having 8 to 11 carbon atoms according to the general formula $(CH_2)_{6-9}.(COOH)_2$ has been found to be particularly suitable; these are suberic acid, azelaic acid, sebacic acid and nonane dicarboxylic acid. From these dicarboxylic acids, which are advisably employed in the form of their sodium or calcium salts, sebacic acid has been found to be most suitable. In the form of an oily film, it offers protection against too rapid evaporation of the lacrimal fluid on the eye. The addition according to the invention of, for example, sebacic acid to conventional eye drops thus retards the evaporation of the dropped-in liquid and increases the oil layer disposed on the surface which is anchored in the aqueous partial layer of the lacrimal film by way of the hydrophilic groups in the dicarboxylic acid.

The object of the present invention is thus the use of dicarboxylic acids having 8 to 11 carbon atoms as an additive in the production of eye drops. The dicarboxylic acids may advisably be employed in the form of their sodium or calcium salts; the use of sebacic acid, particularly in the form of its sodium or calcium salt, has been found to be most advantageous.

Literature is known which discloses the use of dicarboxylic acids, particularly dicarboxylic acids having 7 to 13 carbon atoms, for the treatment of various skin diseases. According to WO-A1-88/00465, these dicarboxylic acids are employed, for example, as topical treatments for rosacea. EP-A2,229,654 relates to the treatment of inflammatory dermatoses, infectious cutaneous diseases and loss of hair as a result of inflammations or hormonal anomalies. U.S. Pat. 4,292,326 employs dicarboxylic acids having 7 to 13 carbon atoms for the treatment of acne, hyperpigmentary dermatoses as well as hyperpigmentations of the skin. Finally, according to U.S. Patent 4,034,077, sebacic acid is employed in concentrations from 2 to 30% as an additive in baby ointments and baby powder to protect against skin irritations when wearing diapers.

These proposed uses of dicarboxylic acids disclosed in the literature, particularly those containing 7 to 13 carbon atoms, relate exclusively to the treatment of skin diseases and thus do not constitute anticipation of the subject matter of the invention.

SUMMARY OF THE INVENTION

The present invention thus discloses and claims use of aliphatic dicarboxlyic acids of the general formula $(CH_2)_{6-9}.(COOH)_2$ and their salts with inorganic bases, respectively, as an additive in the production of eye drops. Use of sodium or calcium salts of aliphatic dicarboxylic acids is preferred. Also preferred is use of sebacic acid and its sodium or calcium salts, respectively.

Eye drops produced according to the invention and containing an additive in the form of sebacic acid have particular advantages in the treatment of "dry eye" (keratoconjunctivitis sicca), because here a longer period of dwell of the wetting liquid on the surface of the eye (cornea, conjunctiva) is of decisive significance for improved efficacy.

Sebacic acid is an aliphatic dicarboxylic acid of the formula $HOOC(CH_2)_8COOH$ which is available in the trade and can be produced as an absolutely pure solution in water by way of ion exchange chromatography (HPLC [high pressure liquid chromatography]).

For the manufacture of eye drops, a stock solution is initially prepared in the following manner:

A suspension of sebacic acid and EDTA (ethylenediaminetetraacetic acid) in water is treated for five minutes in an ultrasonic bath at room temperature; then, 4n NaOH are slowly dripped in under heavy stirring to set a pH of 7.4. In this way, a final sebacic acid concentration of 10% (weight/volume) is obtained as well as a final concentration of EDTA of 0.1% (weight/volume).

For practical application, a 0.5% final concentration of sebacic acid (dilution of the stock solution 1:20) should be employed. For the preparation of the actual eye drops, physiological solutions (e.g. saline) having a pH of 7.0 to 7.5 or mixtures of conventional eye drops and physiological solutions or also undiluted conventional eye drops may serve as the dilution medium.

DESCRIPTION OF THE PREFERRED EMBODIMENTS

The invention will now be described in greater detail by the example below.

EXEMPLARY EMBODIMENT

Production of Eye Drops For The Treatment of Keratoconjunctivitis Sicca

Ready-for-use eye drops are prepared from the following components:

| | |
|---|---|
| sebacic acid stock solution | 1.0 ml |
| *acidum boricum* | 0. 3 ml |
| methyl cellulose solution | 10. 0 ml |
| (0.10 g methyl cellulose, 0.09 g NaCl *puriss. aqua bidest* ad 10 ml) | |
| physiological Nacl solution | ad 19.0 ml |

The addition of sebacic acid stock solution to eye drops employed to treat keratoconjunctivitis sicca (dry eye) patients has been tested in an appropriate group of patients. Of the total of 60 participants in the test, only a single patient did not consider the eye drops to be pleasant, the remaining 59 participants exhibited very good compatibility. At their own request, more than half of the patients were treated continuously over an observation period of two years with the eye drops produced according to the use of the invention.

What is claimed is:

1. A method of extending dwell time of conventional eye drops applied on the surface of an eye, comprising:
   providing an eye drop solution with an additive in an amount effective to extend the dwell time of the eye drop solution on the surface of an eye, the additive comprising at least one substance selected from the group consisting of an aliphatic dicarboxylic acid having a general formula $(CH_2)_{6-9}.(COOH)_2$ and a salt of an aliphatic dicarboxylic acid having a general formula $(CH_2)_{6-9}.(COOH)_2$ with an inorganic base.

2. The method according to claim 1, wherein the at least one salt is selected from the group consisting of a sodium salt and a calcium salt.

3. The method according to claim 1, wherein the aliphatic dicarboxylic acid is selected from the group consisting of suberic acid, azelaic acid, sebacic acid, and nonane dicarboxylic acid.

4. The method according to claim 3, wherein the at least one salt is selected from the group consisting of a sodium salt and calcium salt.

5. The method according to claim 1, wherein the aliphatic dicarboxylic acid is sebacic acid.

6. The method according to claim 5, wherein the at least one salt is selected from the group consisting of a sodium salt and a calcium salt.

7. The method according to claim 1, wherein the eye drop solution has a concentration of the additive of 0.5% (weight/volume).

* * * * *